United States Patent [19]
Castell

[11] Patent Number: 5,900,373
[45] Date of Patent: May 4, 1999

[54] SYSTEM OF INOCULATION OF BIOLOGICAL SAMPLES ONTO THE AGAR SURFACE IN PETRI CAPSULES

[75] Inventor: Victor Font Castell, Barcelona, Spain

[73] Assignee: Iul, S.A., Barcelona, Spain

[21] Appl. No.: 08/842,387

[22] Filed: Apr. 23, 1997

[30] Foreign Application Priority Data

Apr. 23, 1996 [ES] Spain ...................................... 9600918

[51] Int. Cl.[6] .............................. C12M 3/00; G01N 1/00
[52] U.S. Cl. ..................................... 435/286.3; 435/286.4; 435/309.1; 73/863.03
[58] Field of Search ............................. 435/286.3, 286.4, 435/309.1; 73/863, 863.03, 864.91

[56] References Cited

U.S. PATENT DOCUMENTS 4,273,877  6/1981  Anagnostopoulos ..................... 435/293
5,629,201  5/1997  Nugteren ............................... 435/283.1

Primary Examiner—David A. Redding
Attorney, Agent, or Firm—Klauber & Jackson

[57] ABSTRACT

It is done by means of a device inoculating the sample onto the gel of a Petri capsule, the application pressure of the outlet being very light in order not to harm the gel.

It includes a syringe or microsyringe whose ram totally invades the chamber in order not to administer air. After inoculating the sample, the syringe is thrown away and thus conventional washing and rinsing are eliminated. It is mounted in an easily removable manner in a support frame fastened to a swing arm, there being a balancing counterweight.

The syringe is remote controlled, preferably by cable and with an electric motor, by means of bearings, the cable advantageously passing through the swing axis.

6 Claims, 1 Drawing Sheet

SYSTEM OF INOCULATION OF BIOLOGICAL SAMPLES ONTO THE AGAR SURFACE IN PETRI CAPSULES

OBJECT OF THE INVENTION

As expressed in the title of this specification, the present invention refers to a new system of inoculation of biological samples onto the agar surface in Petri capsules, whereby noteworthy advantageous characteristics in relation to the systems that presently exist for this purpose are provided.

The biological sample that is subjected to analysis to carry out the bacteria or microorganism colony count, has to be placed in the so-called Petri capsules, according to a distribution that may or may not be spiral, or according to another distribution, occupying the agar or gel surface that fills the bottom of the Petri capsule, wherein the microorganisms have developed.

A way of carrying out the inoculation of the samples is spirally and it takes places during the rotation of the Petri capsule, thus achieving that there are different concentrations of the sample in the same plate given that as the radial distance increases the concentration decreases.

Agar is the gelatinous medium where microorganisms develop and it has a certain texture that must not be scratched or damaged by the end of the mouth through which inoculation of the sample takes place. The end thereof must also remain in contact with the gel so that there is a true uniform transfer of the sample to be analyzed. It is known that a specific weight of about one gram must not be exceeded. Agar, therefore due to its gelatinous nature, can be easily damaged if the pressure is increased, although it is necessary to overcome the surface tension so that the agar is wet by the sample.

So that this value is not exceeded, the inoculating device forms part of an arm swinging around a cross axis, on the other side of which there is a balancing counterweight.

BACKGROUND OF THE INVENTION

Nowadays, the system of inoculation of biological samples onto the agar surface, suffers from a basic problem and a noteworthy rise in price is derived from it, aside from the fact that the microorganism colony count may be falsified.

This problem consists in that inoculation (whether or not it is spiral) onto the gel of the Petri capsule, requires a duct that is initially run through in the direction of suction so that the sample is lodged in a chamber from which the programmed dose will be poured by means of operating a small cylinder, the sample running the opposite path. The sample admitted for analysis, obviously contained microorganisms and therefore after inoculation, it has to be subjected to a thorough cleaning stage in order to prevent contamination of the next sample. Therefore, the tube that has become dirty with microorganisms, is washed with bleach and then rinsed several times to eliminate the microorganisms, given that if it has not been rinsed thoroughly, the bleach itself kills the microorganisms of the following analysis. This implies a very serious problem that falsifies the count to a larger or smaller degree.

Therefore, a continuous tube that becomes entirely dirty and that has in series a closing or nipping valve and that after being nipped the ram is moved so that the desired amount of liquid comes out, is used in the conventional inoculation system.

DESCRIPTION OF THE INVENTION

In broad outline, in order to solve the inconveniences described in the previous section, as well as to achieve the prerogatives suggested according to the invention, a system of inoculation of biological samples onto the agar surface in Petri capsules, consisting of using as an inoculating device, a syringe or microsyringe that has a ram that entirely fills the chamber of the tube-shaped body of the syringe and that is remote controlled in order to admit the sample, as well as to pour it onto the agar, although, of course, the latter movement is the one that is to be carried out gently and without there being any excess pressure that may damage the gel, as we have indicated above, since the outlet end where the sample comes out must not exert a pressure that exceeds a prefixed value, is proposed.

This microsyringe is filled with the sample and after inoculation is carried out, it is thrown away. For the next analysis a new syringe is used and thus, the imperative and expensive need of washing with bleach and the subsequent rinsing is eliminated, which noticeably reduces the costs of the analysis. Once the syringe is disposed of, there are no more contaminated elements.

The reason why a ram that totally invades the chamber of the syringe or microsyringe is used, is that in this way no air is admitted upon filling the syringe. As no air bubbles are formed, exact amounts are always poured upon carrying out the inoculation. It should be taken into account that in the most diluted turn of the Petri capsule, a tenth of a microliter may be poured, and obviously if there is a little air inside, it is not certain that said amount is being poured. When the tip is applied over a gel, whatever type it is, just with the maximum weight of one gram (or the like), the mouth remains stopped up, without there being excess pressure. If there had been any air inside excess pressure would have been increased and although the ram were to move slightly, liquid might not have been inoculated.

Nowadays there are manual pipettes in this clinical field, that exchange tips, but where the ram is air and therefore, there is no direct physical contact with the biological sample, the inoculation varying upon the ram being of compressed air. The pipette tips are always empty and although only this part fills with the sample liquid, there Is still the problem that the ram is of air and the inoculation is falsified and thus the count.

As to the structure that the inoculating device in question has, by means of the syringe, we can mainly say that the operation of the ram is done by remote control so as not to alter the application pressure of the end of the syringe on the agar. This operation is advantageously done due to its very low cost, by means of a steel cable protected by its corresponding protective cover. The traction and thrust on this cable is carried by a motor and by means of bearings so that only axial pressure is exerted and so that there is no rotational component in the form of turning torque.

The operation of the motor on the cable is optimized, upon making the end portion of the cable pass so that it adopts an axial position with the rotation axis of the inoculating device given that it forms part of a swing arm, balanced with an adjustable counterbalance.

The syringe is blocked in a support frame integral to the end of this swing arm and in such a way that it can be easily removed for disposal and in order to mount a new syringe.

The ram remains fastened to a part anchored to the active end of the operating cable. The way to connect and disconnect the anchor of the ram, in a manner similar to that of the syringe, is also very easy. On its part, the protective cover that protects and guides the operating cable of the ram, remains anchored to the axial recess that exists in the swing axis. The geometric axis also coincides with the direction of movement of the cable, by means of a traction motor or other operating element.

In order to provide a better understanding of the characteristics of the invention and forming an integral part of this specification, a page of drawings in whose sole figure, the following has been represented with an illustrative and non-restrictive manner, is attached.

DESCRIPTION OF THE PREFERRED EMBODIMENT

Figure 1:
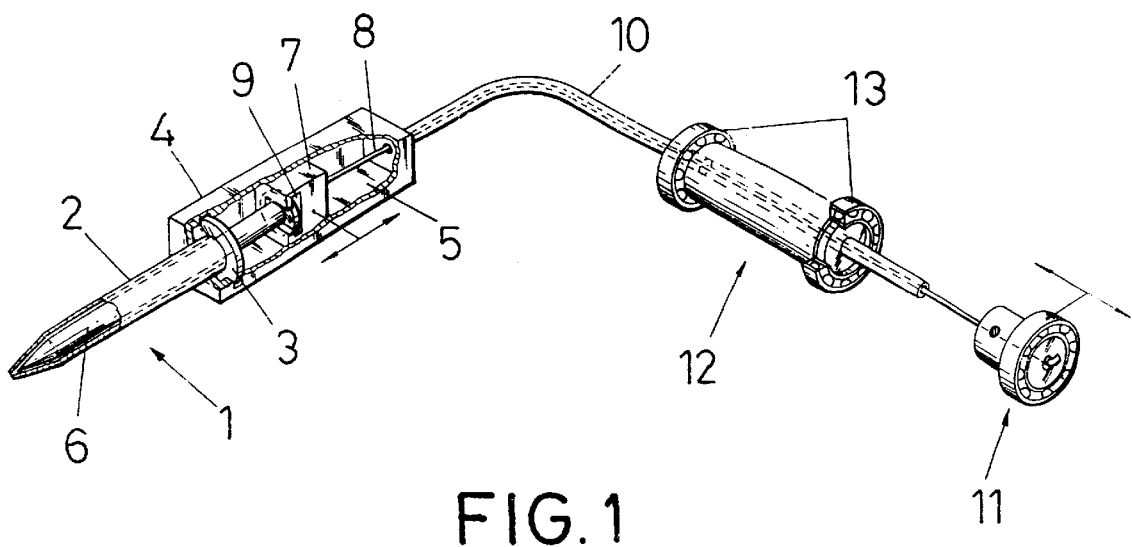
FIG. 1 is a schematic view of the system of inoculation of biological samples onto the agar surface in Petri capsules, according to the invention.

Making reference to the numbering used in the figure, we can see how in this specific embodiment, the inoculation of the biological sample is done by means of a disposable syringe (1), that is thrown away after being used. The body (2) of the syringe (1) and more specifically its rear widened end or fastening flange (3), remains secured to the support frame (4), defining a rear axial recess (5) that allows movement of the ram (6). Part (7) secured to the end of the steel cable (8) that materializes the operating means of the ram moves duly guided in this axial recess (5).

Part (7) has a side window (9) that receives the free and widened end of the ram (6). The syringe (1) may, therefore, be easily assembled and disassembled effecting parallel movement for its lateral insertion in the support frame (4).

Reference (10) designates the protective cover of the cable remote control (8).

The distal end of the operating cable (8), is anchored to a bearing (11) support so that the traction and trust that the operating element (electric motor or the like) is to effect, does not have any rotational element that would provoke an increase or decrease of the pressure exerted by the end of the syringe (1) on the agar surface, as desired.

Reference (12) designates the rotating support that materializes the swing axis of the arm to which the frame (4) holding the syringe (1) is anchored, this arm not being represented because the same may have any desired geometric shape and length. The balancing counterweight that would, of course, go to the other side of the resistance support (12), anchored to another arm, has not been represented either.

The swing support (12) does so by means of bearings (13) and the cable (8) passes through the axial hole thereof and the protective operating cover (10) of the ram (6). The cable (8) and protective cover (10), at the end of the swing axis (12) and up to their connection to the ram (6) and frame (4), respectively, follow a curvilinear path that does not alter the value of the pressure exerted during the axial movement of the axis (8) to relieve the syringe (1) onto the agar surface in the Petri capsule.

I claim:

1. System of sterile inoculation of biological samples onto gel surfaces in Petri capsules that allows for control of quantities of biological samples inoculated onto gel surfaces, wherein said system comprises of:
    a) an inoculating device made up of
        a support frame;
        a disposable syringe, including
            i) a first end
            ii) means for securing the disposable syringe to said support frame in a removable manner;
            iii) a pouring end;
            iv) a chamber for housing said biological sample, said chamber being located between said first end and said pouring end of said disposable syringe;
            v) a ram having a first end and a second end, wherein said ram is movable within said chamber, and wherein the movement of said ram within said chamber is controlled remotely, said ram being movable between a first position and a second position, said ram being arranged to fill the entire chamber of said disposable syringe when said ram is in said second position; and
    b) an operating mechanism arranged to control inoculation of said sample onto said gel surface; wherein said operating mechanism remotely controls movement of said ram within said chamber of said disposable syringe.

2. System according to claim 1, wherein said means for securing said disposable syringe to said support includes a first fastening flange located at said first end of said disposable syringe, and a second fastening flange located at the first end of said ram, and said operating mechanism includes a part having a window, said part being located within said support frame; wherein said first fastening flange may be secured to said support frame, and said second fastening flange may be secured to said window of said part, said operating mechanism controlling movement of said part in said support frame.

3. System of sterile inoculation of biological samples onto gel surfaces in Petri capsules that allows for control of quantities of biological samples inoculated onto gel surfaces, according to claim 2, wherein said operating mechanism further includes a steel cable connected to said part, to which said first end of the ram may be secured, the steel cable being protected and guided in a protective cover secured to the support frame, to which the same is axially immobilized.

4. System of sterile inoculation of biological samples onto gel surfaces in Petri capsules according to claim 3, characterized in that the traction or thrust on said steel cable is exerted by a ball bearing that prevents or minimizes the formation of turning torque on said steel cable, wherein said ball bearing achieves operation by an electric motor.

5. System of sterile inoculation of biological samples onto gel surfaces in Petri capsules, according to any of claims 3, 4, 1 or 2, wherein the support frame is open at the side to allow insertion of the first end comprising a first fastening flange of said disposable syringe, there being an extension of said support frame, said part being guided in said extension.

6. System of sterile inoculation of biological samples onto gel surfaces in Petri capsules that allows for control of quantities of biological samples inoculated onto gel surfaces, wherein said system comprises:
    a) an inoculating device made up of
        a support frame;
        a disposable syringe, including
            i) a first end
            ii) means for securing the disposable syringe to said support frame in a removable manner
            iii) a pouring end;
            iv) a chamber for housing said biological sample, said chamber being located between said first end and said pouring end of said disposable syringe;
            v) a ram having a first end and a second end, wherein said ram is movable within said chamber, and wherein the movement of said ram within said chamber is controlled remotely, said ram being movable between a first position and a second position, said ram being arranged to fill the entire chamber of said disposable syringe when said ram is in said second position;

wherein said means for securing said disposable syringe to said support includes a first fastening flange located at said first end of said disposable syringe, and a second fastening flange located at the first end of said ram, and said support frame is open at the side to allow insertion of the first end comprising a first fastening flange of said disposable syringe, there being an extension of said support frame, and a part having a window, wherein said part is located within said support frame;

b) an operating mechanism arranged to control inoculation of said sample onto said gel surface; wherein said operating mechanism remotely controls movement of said ram within said chamber of said disposable syringe; wherein said first fastening flange may be secured to said support frame, and said second fastening flange may be secured to said window of said part, said operating mechanism controlling movement of said part in said support frame with a steel cable connected to said part, to which said first end of the ram may be secured, the steel cable being protected and guided in a protective cover secured to the support frame, to which the same is axially immobilized, such that the traction or thrust on said steel cable is exerted by a ball bearing that prevents or minimizes the formation of tuning torque on said steel cable, wherein said ball bearing achieves operation by an electric motor.

* * * * *